(12) United States Patent
Shekalim et al.

(10) Patent No.: US 12,268,828 B2
(45) Date of Patent: Apr. 8, 2025

(54) DOUBLE CONCENTRIC GUIDEWIRE

(71) Applicant: MICROBOT MEDICAL LTD., Caesarea (IL)

(72) Inventors: Avraham Shekalim, Nesher (IL); Noam Peleg, Gan Ner (IL)

(73) Assignee: CARDIOSERT LTD., Nesher (IL)

( * ) Notice: Subject to any disclaimer, the term of this patent is extended or adjusted under 35 U.S.C. 154(b) by 867 days.

(21) Appl. No.: 15/748,658

(22) PCT Filed: Aug. 18, 2016

(86) PCT No.: PCT/IL2016/050907
§ 371 (c)(1),
(2) Date: Jan. 30, 2018

(87) PCT Pub. No.: WO2017/033182
PCT Pub. Date: Mar. 2, 2017

(65) Prior Publication Data
US 2018/0214675 A1    Aug. 2, 2018

Related U.S. Application Data

(60) Provisional application No. 62/208,715, filed on Aug. 23, 2015.

(51) Int. Cl.
*A61M 25/09*    (2006.01)
(52) U.S. Cl.
CPC ......... *A61M 25/09041* (2013.01); *A61M 2025/09083* (2013.01); *A61M 2025/09116* (2013.01); *A61M 2025/0915* (2013.01)
(58) Field of Classification Search
None
See application file for complete search history.

(56) References Cited

U.S. PATENT DOCUMENTS

| | | |
|---|---|---|
| 4,676,249 A | 6/1987 | Arenas et al. |
| 4,917,102 A | 4/1990 | Miller et al. |

(Continued)

FOREIGN PATENT DOCUMENTS

| | | |
|---|---|---|
| CA | 2867460 | 9/2013 |
| WO | 2003018085 | 3/2003 |

(Continued)

OTHER PUBLICATIONS

TruePath(TM) "CTO Device Directions For Use" 2012. Boston Scientific.

(Continued)

*Primary Examiner* — Aurelie H Tu
(74) *Attorney, Agent, or Firm* — Rivka Friedman

(57) ABSTRACT

A double guide wire includes two guidewires deployed concentrically, one within the other. Each guidewire is formed as an elongated flexible shaft having a distal portion including a deflectable helical coil terminating at a distal tip. The first guidewire is implemented as a hollow guidewire having a central lumen extending along its length, while the second guidewire is configured as a smaller gauge guidewire deployed within the central lumen of the first guidewire. An adjuster mechanism allows the inner guidewire to be advanced and retracted relative to the outer guidewire, transforming the guidewire between: a first state in which the distal tip of the second guidewire is adjacent to the distal tip of the first guidewire; and a second state in which at least part of the distal portion of the inner guidewire is advanced beyond the distal tip of the first guidewire.

15 Claims, 16 Drawing Sheets

(56) References Cited

U.S. PATENT DOCUMENTS

| | | | |
|---|---|---|---|
| 5,040,543 A | 8/1991 | Badera et al. | |
| 5,133,364 A * | 7/1992 | Palermo | A61M 25/0905 |
| | | | 600/434 |
| 5,346,473 A | 9/1994 | Bowman | |
| 5,356,388 A | 10/1994 | Sepetka et al. | |
| 5,456,667 A * | 10/1995 | Ham | A61M 25/0074 |
| | | | 604/104 |
| 5,527,298 A | 6/1996 | Vance et al. | |
| 5,605,162 A | 2/1997 | Mirzaee et al. | |
| 5,908,395 A | 6/1999 | Stalker et al. | |
| 5,928,191 A | 7/1999 | Houser et al. | |
| 5,944,689 A * | 8/1999 | Houser | A61B 18/1492 |
| | | | 604/95.04 |
| 5,968,064 A | 10/1999 | Selmon et al. | |
| 5,993,424 A | 11/1999 | Lorenzo et al. | |
| 6,026,834 A | 2/2000 | Azima | |
| 6,059,767 A | 5/2000 | Noriega | |
| 6,113,557 A | 9/2000 | Fagan | |
| 6,428,489 B1 | 8/2002 | Jacobsen et al. | |
| 6,755,794 B2 | 6/2004 | Soukup | |
| 6,805,676 B2 | 10/2004 | Klint | |
| 6,824,550 B1 | 11/2004 | Noriega et al. | |
| 7,381,198 B2 | 6/2008 | Noriega et al. | |
| 7,402,151 B2 | 7/2008 | Rosenman et al. | |
| 7,481,778 B2 | 1/2009 | Cedro et al. | |
| 7,491,224 B2 | 2/2009 | Cox et al. | |
| 7,628,763 B2 | 12/2009 | Noriega et al. | |
| 7,713,215 B2 | 5/2010 | Shriver | |
| 8,043,312 B2 | 10/2011 | Noriega et al. | |
| 8,043,314 B2 | 10/2011 | Noriega et al. | |
| 8,353,922 B2 | 1/2013 | Noriega et al. | |
| 8,496,680 B2 | 7/2013 | Noriega et al. | |
| 8,747,332 B2 | 6/2014 | Noriega et al. | |
| 9,113,955 B2 | 8/2015 | Noriega et al. | |
| 9,233,225 B2 | 1/2016 | Hebert | |
| 9,254,143 B2 | 2/2016 | Huynh et al. | |
| 9,387,308 B2 | 7/2016 | Hinchliffe et al. | |
| 2002/0095102 A1 | 7/2002 | Winters | |
| 2003/0088262 A1 | 5/2003 | Mich | |
| 2003/0139689 A1 | 7/2003 | Shturman et al. | |
| 2005/0020993 A1 | 1/2005 | Bonnette et al. | |
| 2005/0119615 A1 | 6/2005 | Noriega et al. | |
| 2005/0288695 A1 | 12/2005 | Jenson et al. | |
| 2006/0074442 A1 | 4/2006 | Noriega et al. | |
| 2006/0106348 A1 * | 5/2006 | Lichtenberg | A61M 25/0631 |
| | | | 604/164.08 |
| 2006/0167417 A1 * | 7/2006 | Kratz | A61M 25/0668 |
| | | | 604/164.05 |
| 2006/0200191 A1 | 9/2006 | Zadno-Azizi | |
| 2006/0293612 A1 | 12/2006 | Jenson et al. | |
| 2007/0002168 A1 | 1/2007 | Depen et al. | |
| 2007/0021685 A1 * | 1/2007 | Oepen | A61M 25/09 |
| | | | 600/585 |
| 2008/0064989 A1 * | 3/2008 | Chen | A61M 25/09 |
| | | | 600/585 |
| 2008/0281228 A1 | 11/2008 | Parodi et al. | |
| 2009/0125045 A1 | 5/2009 | Heuser | |
| 2009/0198153 A1 | 8/2009 | Shriver | |
| 2009/0259298 A1 * | 10/2009 | Mayberry | A61F 2/97 |
| | | | 623/1.35 |
| 2009/0312747 A1 | 12/2009 | Delaney | |
| 2010/0087780 A1 | 4/2010 | Tekulve | |
| 2010/0094143 A1 | 4/2010 | Mahapatra et al. | |
| 2010/0298922 A1 | 11/2010 | Thornton et al. | |
| 2010/0305475 A1 | 12/2010 | Hinchliffe et al. | |
| 2011/0245808 A1 * | 10/2011 | Voeller | A61M 25/0013 |
| | | | 604/528 |
| 2012/0330335 A1 * | 12/2012 | Shekalim | A61B 17/22012 |
| | | | 606/159 |
| 2013/0172855 A1 * | 7/2013 | Wood | A61M 25/09 |
| | | | 604/528 |
| 2013/0289445 A1 * | 10/2013 | Edamatsu | A61M 25/09 |
| | | | 600/585 |
| 2014/0121642 A1 | 5/2014 | Jordan et al. | |
| 2014/0135736 A1 * | 5/2014 | Hebert | A61M 25/0138 |
| | | | 604/525 |
| 2014/0343457 A1 | 11/2014 | Shekalim et al. | |
| 2017/0049514 A1 * | 2/2017 | Cosman | A61N 1/0551 |
| 2018/0317949 A1 * | 11/2018 | Lenker | A61B 17/32053 |

FOREIGN PATENT DOCUMENTS

| | | |
|---|---|---|
| WO | 2006058223 | 6/2006 |
| WO | 2007095498 | 8/2007 |
| WO | 2009002971 A1 | 12/2008 |
| WO | 2012096816 | 7/2012 |
| WO | 2013118105 | 8/2013 |

OTHER PUBLICATIONS

Hee-Yeol Kim: "Percutaneous Recanalization of Coronary Chronic Total Occlusions: Current Devices and Specialized D Wire Crossing Techniques" Korean Circ J. May 2010; 40(5): 209-215.

Carlino, et al (2008) CTO Recanalization by Intraocclusion Injection of Contrast: The Micochannel Technique, Catheterizaiton and Cardiovascular Interventions, vol. 71, Issue 1, pp. 20-26.

* cited by examiner

DOUBLE CONCENTRIC GUIDEWIRE

FIELD AND BACKGROUND OF THE INVENTION

The present invention relates to medical devices for interventional cardiology, radiology and vascular surgery. More specifically, it relates to a guidewire for use in such procedures.

Referring to U.S. Pat. No. 5,968,064 (Selmon at el, 1997), stenosis is narrowing or obstruction of the interior passage of an artery. This condition, known generally as an occlusion, is found in patients suffering from atherosclerosis (accumulation of fibrous, fatty or calcified tissue in the arteries). An occlusion can manifest itself in hypertension (high blood pressure), ischemia (deficiency of circulation), angina (chest pain), myocardial infarction (heart attack), stroke, or death. An occlusion may be partial or total, may be soft and pliable or hard and calcified, and may be found at a great variety of sites in the arterial system including the aorta, the coronary and carotid arteries and peripheral arteries.

In patients suffering from severe or total arterial occlusion ("chronic total occlusion" or CTO), it is preferable to open the severely or totally occluded artery itself, rather than perform a bypass. If a guide wire and working catheter can be passed through or around the atheroma, the severe or total occlusion can be treated by percutaneous transluminal coronary angioplasty (PTCA), directional coronary atherectomy (DCA), stenting, site-specific drug delivery or a combination of these proven therapies.

In order to perform these procedures, a guidance system is used in conjunction with coronary catheterization. One of these guidance systems is biplane fluoroscopy, wherein the interventionist observes two flat real-time x-ray images acquired from different angles. When using an imaging technique the patient is exposed to a relatively large amount of x-ray radiation. Intensive exposure to x-ray increases risk of cancer. In addition, in order to achieve an image of the blood vessels, during the procedure, dosage of x-ray contrast media are injected to the patient vessels through guide catheters. The contrast media has some degree of toxicity depending on its physiochemical properties such as hydrophilicity/lipophilicity and protein binding ability. Because of these risks, it is of great interest to reduce the medical intervention time to a minimum.

Devices intended for CTO crossing via atherectomy were developed in the recent years. For example: Crosser™, Frontrunner™ and TruePath™. Crosser™ (Bard Peripheral Vascular, Inc.) is a 3.9 F catheter that utilizes high-frequency mechanical vibration to cross CTOs. Frontrunner™ (Cordis Corporation) is a 3.1 F catheter with actuating distal tip that creates a channel through occlusions via blunt microdissection. TruePath™ (Boston Scientific Corporation) having a 0.018-inch (1.4 F) shaft profile creates a microdissection through CTOs via powered rotation of an inner drive shaft having a diamond-coated, 0.017-inch, rotating abla-tive tip. Crossing via atherectomy requires a device having a cutting tip stiff enough to make dissections through the calcified plaque of the CTO proximal cap. For safety reasons, in order to reduce risk of damaging and perforating the vessel wall, an accurate positioning of the device within the lesion is required. Their stiff tips prevent those devices from being manipulated easily to steer and navigate within the lesion. Crosser™ and the Frontrunner™ are advanced over a guide wire that position the tool. Advancing the tool requires manipulating the guide wire though the lesion that in turn makes the crossing procedure cumbersome. The tip of the TruePath™ is floppy enough to be steered within relatively straight and large peripheral vessels but on the other hand it is too stiff to use in the tortuous geometry of the coronary vessels.

A CTO often starts as a ruptured plaque with bidirectional thrombus formation. With time, the thrombus and lipid are replaced at first by collagen and later also by calcium. The fibrous tissue is particularly dense at the proximal and distal ends of the lesion, creating fibrous caps surrounding a softer core of organized thrombus and lipid. Histological examination of CTOs has identified that the majority have intraluminal microchannels which can vary in size from 100-500 um. Strauss et al. have proposed that these intraocclusion microvessels may provide a pathway for guidewire crossing of a CTO. (CTO *Recanalization by Intraocclusion Injection of Contrast: The Microchannel Technique*, Carlino et al, Catheterization and Cardiovascular Interventions Volume 71, Issue 1, pages 20-26, 1 Jan. 2008). Crossing CTO via microchannels is safer than atherectomy as it involves just a guide wire with a non-traumatic tip.

In order to negotiate microchannels, the guide wire should have a thin floppy tip with a diameter smaller than the conventional 0.014" tips, preferably below 0.009". The tip should be of a small curve (bend of about 30° 1-2 mm from the end) as a larger curve may hurt the vessel wall during direction control. But, as explained below, in order to navigate in the vascular system, the size (radius) of the curve should be just larger than the vessel lumen diameter.

A distal tip of a guide wire is pre-shaped to form a curve or it is shapeable such that a physician can shape the tip to form a curve. Due to its curved shape, the floppy tip is pressed gently against the vessel walls. By rotating and by moving the guide wire axially, the floppy tip is advanced along the vessel walls. Once the tip reaches the ostium (opening) of a branch in the vascular system, it falls into the branch. In this situation, pushing the guide wire further will cause the tip to advance along the branch.

Therefore, a 0.014" floppy guide wire with a relatively large curve is used to navigate to and first negotiate the lesion. However, this type of curve is not suitable to negotiate a CTO lesion and as CTO lesions usually consist of a heavily calcified proximal portion (designated as the proximal cap), this floppy guide wire could not pass through.

In order to cross the lesion, the physician may typically switch to a CTO guide wire with a stiffer and smaller-curve tip and try to cross by manipulating this wire. If this wire fails to cross the lesion, the physician may switch this wire with a still stiffer one. The physician repeatedly switches between wires, attempting to cross with stiffer and stiffer guide wires. This method is wasteful in terms of time, x-ray exposure and contrast media consumption.

When switching wires, the physician also typically loses his position within the vessel. This in turn reduces his or her chances to successfully cross the lesion.

Stiff guide wires usually include a tapered tip with a diameter that goes down to 0.009 or 0.008 inches. The tapered tip is intended to allow manipulating the tip within micro channels that are part of the proximal cap morphology. However, the combination of a tapered end and a stiff tip increases the risk of perforation by using these wires, so the physician usually limits use of a stiff wire to locations next to or within the CTO. Once the lesion is crossed, the physician would prefer to switch back to a floppy guide wire, although a further switch is again time consuming.

In order to increase stiffness and provide support to the guide wire tip the physician may use a micro catheter. By bringing the tip of the micro catheter closer to the tip of the wire the physician gradually increases the wire stiffness. Nevertheless, it is hard to precisely adjust stiffness by this method as the position between the guide wire and the micro catheter needs to be accurately set. Therefore, the guide wire could easily get much stiffer than intended by the physician. This in turn could raise a risk of perforating the vessel.

In case the vessel is totally occluded, contrast media cannot flow beyond the occluded segment. As a result, the following segments of the vessels are not visible in the x-ray images and the physician has to direct the path of the stiff guide wire through the occlusion based on his knowledge and experience. If blood escapes the artery through accidental perforation and accumulates in the pericardial space, it compresses the heart, requiring emergency intervention to avert heart failure and death.

SUMMARY OF THE INVENTION

The present invention is a double guidewire.

According to the teachings of the present invention there is provided a double guidewire comprising: (a) a first guidewire comprising an elongated flexible shaft having a distal portion that terminates in a distal tip, the distal portion comprising a deflectable helical coil, the first guidewire being a hollow guidewire having a central lumen extending along a length of the first guidewire; (b) a second guidewire comprising an elongated flexible shaft having a distal portion that terminates in a distal tip, the distal portion comprising a deflectable helical coil, the second guidewire being deployed within the central lumen of the first guidewire; and (c) an adjuster mechanism mechanically linked to proximal portions of the first and second guidewires, the adjuster mechanism being operable to displace the second guidewire longitudinally relative to the first guidewire between: (i) a first state in which the distal tip of the second guidewire is adjacent to the distal tip of the first guidewire, and (ii) a second state in which at least part of the distal portion of the second guidewire is advanced beyond distal tip of the first guidewire.

According to a further feature of an embodiment of the present invention, the adjuster mechanism is further operable to displace the second guidewire longitudinally relative to the first guidewire to a third state in which the distal tip of the second guidewire is withdrawn proximally along the central lumen so as to leave empty a part of the central lumen along at least part of the distal portion of the first guidewire.

According to a further feature of an embodiment of the present invention, a region of the distal portion adjacent to the distal tip of each of the first and second guidewires is configured to be inelastically deformable or preshaped to impart a lateral deflection to the distal portion, and wherein, when a first length of the distal portion adjacent to the distal tip of each of the first and second guidewires is deflected, partial withdrawal of the second guidewire from the first state towards the third state causes a second length of the double guidewire to be deflected, the second length being longer than the first length.

According to a further feature of an embodiment of the present invention, an external surface of the distal portion of the first guidewire is coated with a hydrophilic coating, and wherein an external surface of the distal portion of the second guidewire is not coated with the hydrophilic coating.

According to a further feature of an embodiment of the present invention, the first guidewire further comprises a metal strip extending along an inner surface of the helical coil and permanently attached to the helical coil at a plurality of spaced-apart locations along the helical coil.

According to a further feature of an embodiment of the present invention, the second guidewire further comprises a tapered metal core extending within the helical coil and permanently attached to the helical coil at the distal tip.

According to a further feature of an embodiment of the present invention, an outer diameter of the first guidewire is sized for use with "014 compatible" over-the-wire devices.

According to a further feature of an embodiment of the present invention, an outer diameter of the first guidewire is sized for use with "038 compatible" over-the-wire devices.

There is also provided according to the teachings of an embodiment of the present invention, a method of performing a surgical procedure on a patient comprising the steps of: (a) providing a double guidewire according to claim 1 with a region of the distal portion adjacent to the distal tip of each of the first and second guidewires having a lateral deflection, the deflected portion of the first guidewire having a first length; (b) introducing the double guidewire into the vascular system of the patient and navigating the double guidewire within the vascular system to reach a location of a lateral branch vessel; and (c) selectively displacing the second guidewire relative to the first guidewire so as to locate deflected portions of the first and second guidewires longitudinally displaced relative to each other, thereby imparting to the double guide wire a lateral deflection extending for a second length, the second length being greater than the first length, to facilitate navigation of the double guidewire into the lateral branch vessel.

According to a further feature of an embodiment of the present invention, the second guidewire is selectively displaced relative to the first guidewire so that the distal portion of the second guidewire extends beyond the distal tip of the first guidewire.

According to a further feature of an embodiment of the present invention, an "014-compatible" over-the-wire device selected from the group consisting of: an angioplasty balloon and an expandable stent, is advanced along the double guidewire.

BRIEF DESCRIPTION OF THE DRAWINGS

The invention is herein described, by way of example only, with reference to the accompanying drawings, wherein.

DESCRIPTION OF THE PREFERRED EMBODIMENTS

Figure 1:
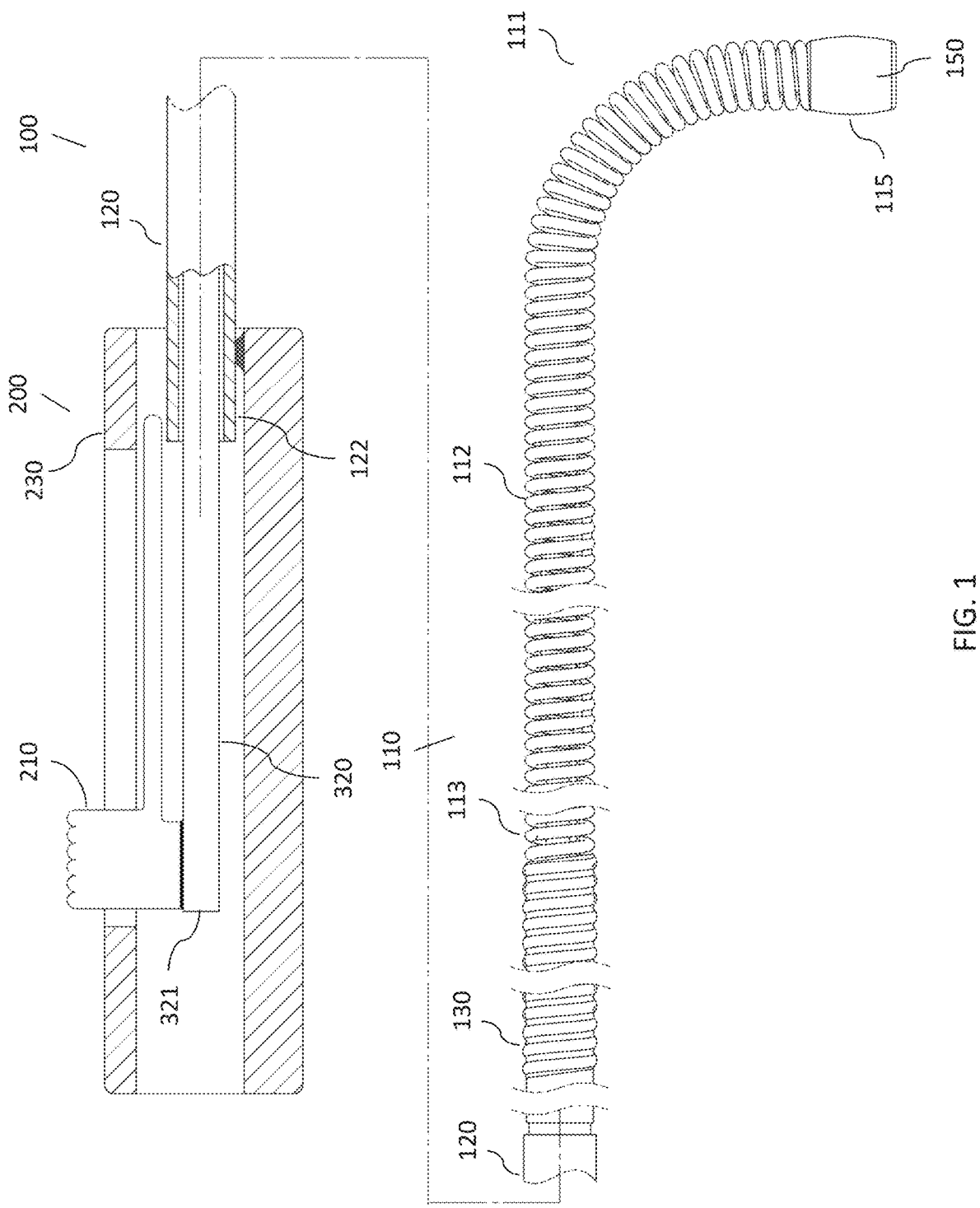
FIG. 1 illustrates a preferred embodiment of the invention, including a schematic section of a manual control handle located at the proximal end of a double guidewire having a controlled tip.

The present invention is a double concentric guidewire.

The principles and operation of guidewires according to the present invention may be better understood with reference to the drawings and the accompanying description.

By way of introduction, it should be noted that certain preferred embodiments of the present invention are distinguished by providing a double guide wire in which two guidewires, each providing a set of features required of a guidewire, are deployed concentrically, one within the other. Thus, each is formed as an elongated flexible shaft having a distal portion that terminates in a distal tip, where the distal portion includes a deflectable helical coil. The helical coil is a critical feature of the distal portion of a guidewire, providing a combination of an easily deflectable structure which can readily negotiate meandering paths while at the same time allowing application of considerable axial force when the coils of the coil are closed against each other. The first guidewire is implemented as a hollow guidewire having a central lumen extending along its length, while the second guidewire is configured as a smaller gauge guidewire deployed within the central lumen of the first guidewire.

An adjuster mechanism, which is typically implemented as a manually-controlled slider integrated with a handle of the double guidewire, allows the second, inner guidewire to be advanced and retracted relative to the first, outer guidewire, thereby providing the user with a range of variations of the properties of the guidewire tip which can typically otherwise only be achieved by swapping guidewires (removing the first one from the body and inserting an alternative one), with all the disadvantages of such replacement as discussed above. Specifically, by operating the adjuster mechanism, the user can preferably transform the guidewire at will between two or more of the following states:

- A first state (FIG. 9) in which the distal tip of the second guidewire is adjacent to the distal tip of the first guidewire. In this state, both guidewires contribute to the stiffness of the guidewire, providing a relatively stiff guidewire, and the effective tip diameter of the guidewire is that of the larger outer guidewire.
- A second state (FIGS. 6-8) in which at least part of the distal portion of the second (inner) guidewire is advanced beyond distal tip of the first guidewire. In this state, the properties of the distal portion of the overall guidewire are defined by the properties of the inner guidewire alone, providing relatively finer gauge and more flexible leading portion of the guidewire.
- A third state (FIGS. 1, 2A, 10, 11 and 13-16) in which the distal tip of the second (inner) guidewire is withdrawn proximally along the central lumen so as to leave empty a part of the central lumen along at least part of the distal portion of the first guidewire. The withdrawal of the inner guidewire from the distal portion of the outer guidewire may be used to extend a length of the distal tip which undergoes deflection, as will be described further below with reference to FIGS. 14-16. Additionally, or alternatively, it may be used to enhance the flexibility of the distal portion of the first guidewire.

The ability to switch between the first and second states described above allows the user to swap as desired between other properties that may be provided by the first and second guidewires. For example, according to one particularly preferred non-limiting example, the external surface of the distal portion of the first (outer) guidewire is coated with a hydrophilic coating, while the external surface of the distal portion of the second (inner) guidewire is not coated with the hydrophilic coating, being either uncoated or having some other coating, such as a hydrophobic coating. This facilitates smooth insertion of the guidewire in the first state, where the properties distal end of the guidewire are defined by the outer guidewire, and the hydrophilic coating ensures greatly reduced friction compared to an uncoated guidewire. When the user is approaching the target location or otherwise needs enhanced tactile feedback, the relatively higher friction second guidewire is advanced so that the outer surface without a hydrophilic coating becomes the leading exposed guidewire surface, thereby providing the desired enhanced tactile feedback.

In order to maintain the structural integrity of the first (outer) guidewire, and as a safety feature, the first guidewire preferably includes a metal strip (shaping ribbon) extending along an inner surface of the helical coil and permanently attached (e.g., welded) to the helical coil at a plurality of spaced-apart locations along the helical coil.

The inner (second) guidewire is preferably formed with a tapered metal core that extends within the helical spring, and is permanently attached (e.g., welded) to the helical coil at the distal tip. The tapering of the metal core inherently provides gradually varying stiffness to the second guidewire, where the distal end is the most floppy part, becoming gradually stiffer with increasing distance from the tip.

The double guidewire of the present invention may be used to advantage in a wide range of applications. By way of one particularly preferred set of applications, the double guidewire is used in procedures performed in the coronary arteries. For such applications, an outer diameter of the first (outer) guidewire is sized for use with "014 compatible"

over-the-wire devices, i.e., with an outer diameter no greater than about 0.014 inch (0.36 mm).

In other applications in the peripheral vascular system, implementations of the invention may employ an outer diameter of the first (outer) guidewire sized for use with "038 compatible" over-the-wire devices, i.e., with an outer diameter no greater than about 0.038 inch (0.97 mm).

A preferred embodiment of the invention, as illustrated in FIG. 1, includes a Guide Wire (100) intended to facilitate the placement of a catheter during vascular intervention procedure. A typical catheter, such as a balloon dilatation catheter (not shown in figures), is not steerable or maneuverable, and therefore it cannot reach the desire location by itself. In order to deliver the dilatation balloon to the desired location in the vascular system at least part of the catheter is introduced over the Guide Wire (100).

The Guide Wire (100) is hollow and has a distal portion (110) terminating at a distal tip (111) and a proximal portion (120) associated with a handle (200).

Figure 2:
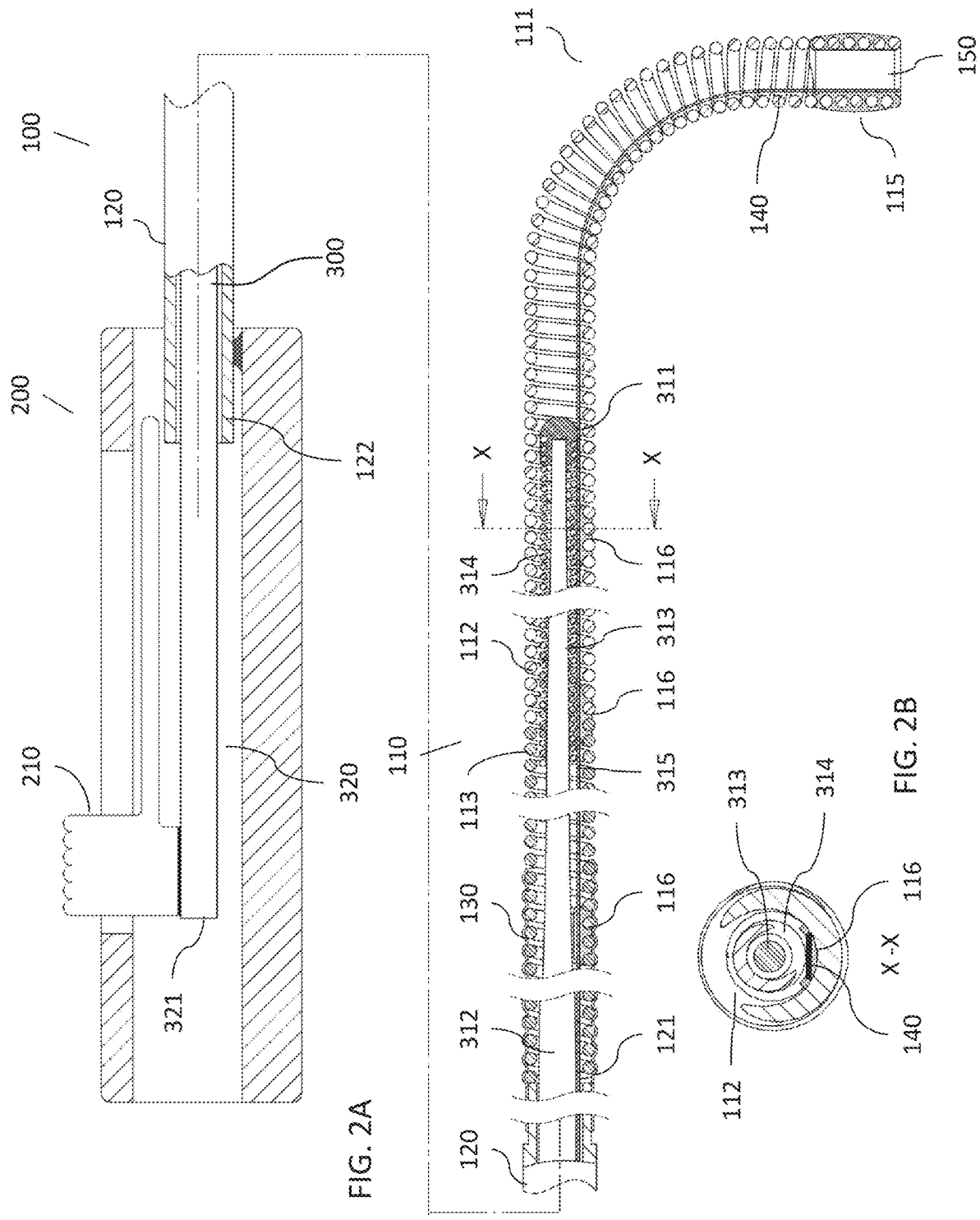
FIGS. 2A and 2B are schematic longitudinal and transverse cross-sections of the distal portion including the tip of the double guidewire of FIG. 1.

As illustrated in FIGS. 2A and 2B the distal portion (110) preferably includes two coils joined to each other: a distal coil (112) made of radio opaque material such as (but not limited to) platinum/tungsten alloy and a proximal coil (113) made of high elastic material such as (but not limited to) spring temper stainless steel. The distal tip (111) of the distal portion is located within the radio opaque coil (112). The proximal portion (120) is a hypotube made of high elastic material such as (but not limited to) spring temper stainless steel or super elastic Nitinol. The distal end (121) of the proximal portion (120) and the proximal end of the distal portion (110) are permanently joined together by welding, soldering, adhering, or any other suitable method. In preferred embodiments, in order to improve the torqueability of the guide wire, the distal end of the proximal portion (120) and part of the distal portion (110) are covered with polymeric heat shrink sleeve (130) made of materials such as (but not limited to) PET or PTFE.

According to FIGS. 2A and 2B, a shaping ribbon (140) is located within the distal portion (110). The distal end of the ribbon is attached to the end (115) of the distal tip (111) and to other points (116) along the distal portion. The ribbon prevents the coils of the distal portion from stretching and therefore it enhances the torqueability of the Guide Wire (100). Most preferably, shaping ribbon (140) is implemented as part of a metal strip which extends along the entire length of the outer guidewire, attached at spaced-apart locations along the guidewire, serving also as a safety ribbon to prevent any part of the guidewire from separating from the rest of the guidewire, even in the event of a mechanical failure. The shaping ribbon (140) is made of high elastic material such as (but not limited to) spring temper stainless steel, Cobalt alloys (such as L605) and Super elastic Nitinol.

Attachment of the metal strip at spaced-apart locations along the guidewire may be achieved by temporarily pressing the strip against the internal surface of the outer guidewire by temporary insertion of an inner rod formed from or coated with a non-stick coating, such as Teflon™ (PTFE), thereby pressing the strip outwards against the inner surface of the outer guidewire, and then employing a suitable bonding technique, such as welding, to form a permanent connection between the outer guidewire and the metal strip. The temporary inner rod is then removed and the inner guidewire is introduced.

The proximal portion (120) is associated with a handle (200). Its proximal end is held by the handle (200) such that it can be turned about its longitudinal axis by using the handle as a torquer. According to a preferred embodiment illustrated in FIG. 4, the handle includes a cutter (220) to cut the proximal portion (120) to remove the handle (200), for example, in order to facilitate placement of a catheter over the Guide Wire.

Turning back to FIG. 1, the distal tip (111) is pre-shaped to form a curve or it is shapeable such that a physician can shape the distal tip (111) to form a curve. The curved tip (111) enables the physician to steer the Guide Wire (100) through the vascular system. In order to steer the tip (111) with safety and efficacy, the distal portion (110) should be on one hand floppy and soft to deflection and on the other hand stiff to torsion such that it transmits torque in one-to-one ratio. Due to its curved shape the floppy tip (111) is pressed gently against the vessel walls (not shown in figures).

By rotating the Guide Wire (100) and by moving it axially the floppy tip (111) moves along the vessels walls. Once the tip reaches the ostium (opening) of a branch in the vascular system it falls into the branch. In this situation, pushing the Guide Wire (100) further will cause the tip (111) to advance along the branch. Using this method the physician can steer the distal tip (111) to almost any desired location in the vascular system.

Figure 3:
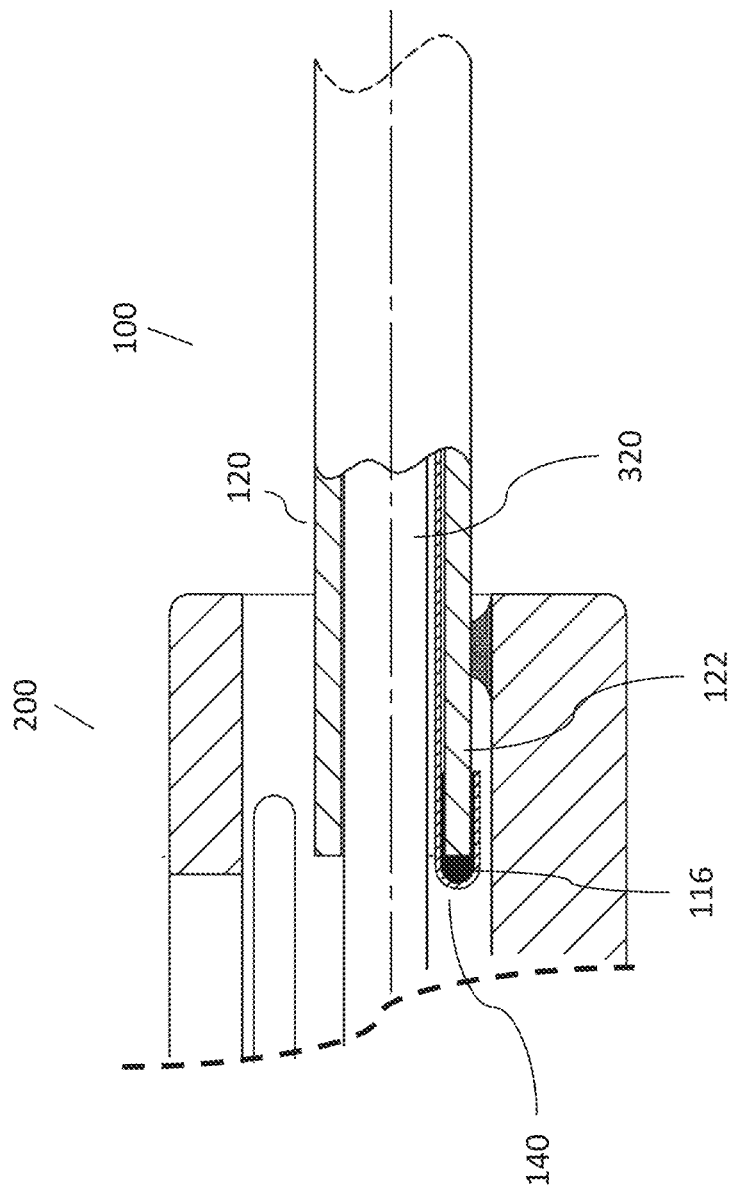
FIG. 3. is a detailed view of the schematic cross section of handle of FIG. 2A where a safety ribbon connected to the proximal end of the guide wire.

The hollow Guide Wire (100) defines a lumen (150) extending along its entire length from the proximal end (122) of the proximal portion (120) to the distal end (115) of the tip (111) of the distal portion (110). In preferred embodiments illustrated in FIGS. 2A-2B and FIG. 3, in order to enhance safety, the shaping ribbon (140) extends along the entire length of the Guide Wire (100) and is attached to the proximal end (122) of the proximal portion (120), and preferably also at other locations spaced apart along the guidewire's length, so that, if for some reason a joint between any portions or components of the Guide Wire (100) were to fail, the ribbon (140) would still hold the whole package together allowing the physician to safely withdraw the Guide Wire (100). A single metal strip thus preferably functions both as a "shaping ribbon" and as a "safety ribbon".

As illustrated in FIG. 2A, a second inner guide wire (300) extends through the lumen (150) from the handle (200) to the distal portion (110). The second guide wire (300) is slidably received within the lumen (150). The second guide wire (300) has a distal portion (310) terminating at a distal tip (311) and a proximal portion (320) associated with handle (200).

As illustrated in FIG. 2A the distal portion (310) of the inner guide wire (300) consists of a core wire (312) having a tapered end (313) placed within an inner distal coil (314). The distal end of the inner coil (314) is attached to the distal end of the core wire (312). The proximal end (315) of the inner coil (314) is also attached to the tapered portion (313) of the core wire (312). The components of the second inner guide wire (300) are made of highly elastic materials such as (but not limited to) spring tempered stainless steel, Cobalt alloys (such as L605) and Super elastic Nitinol. The inner coil (314) is preferably made of radio opaque material such as (but not limited to) platinum/tungsten alloy. In preferred embodiments the core wire (312) is coated with PTFE or other suitable coating to reduce friction.

The proximal portion (320) of the second guide wire (300) is associated with side handle (200) by a slider member (210). The proximal end (321) is attached to the slider by using welding soldering, adhering or any other suitable method. By sliding the slider member (210) along the handle (200) the physician can displace the second inner guide wire (300) within the lumen (150) of the Guide Wire (100).

Figure 6:
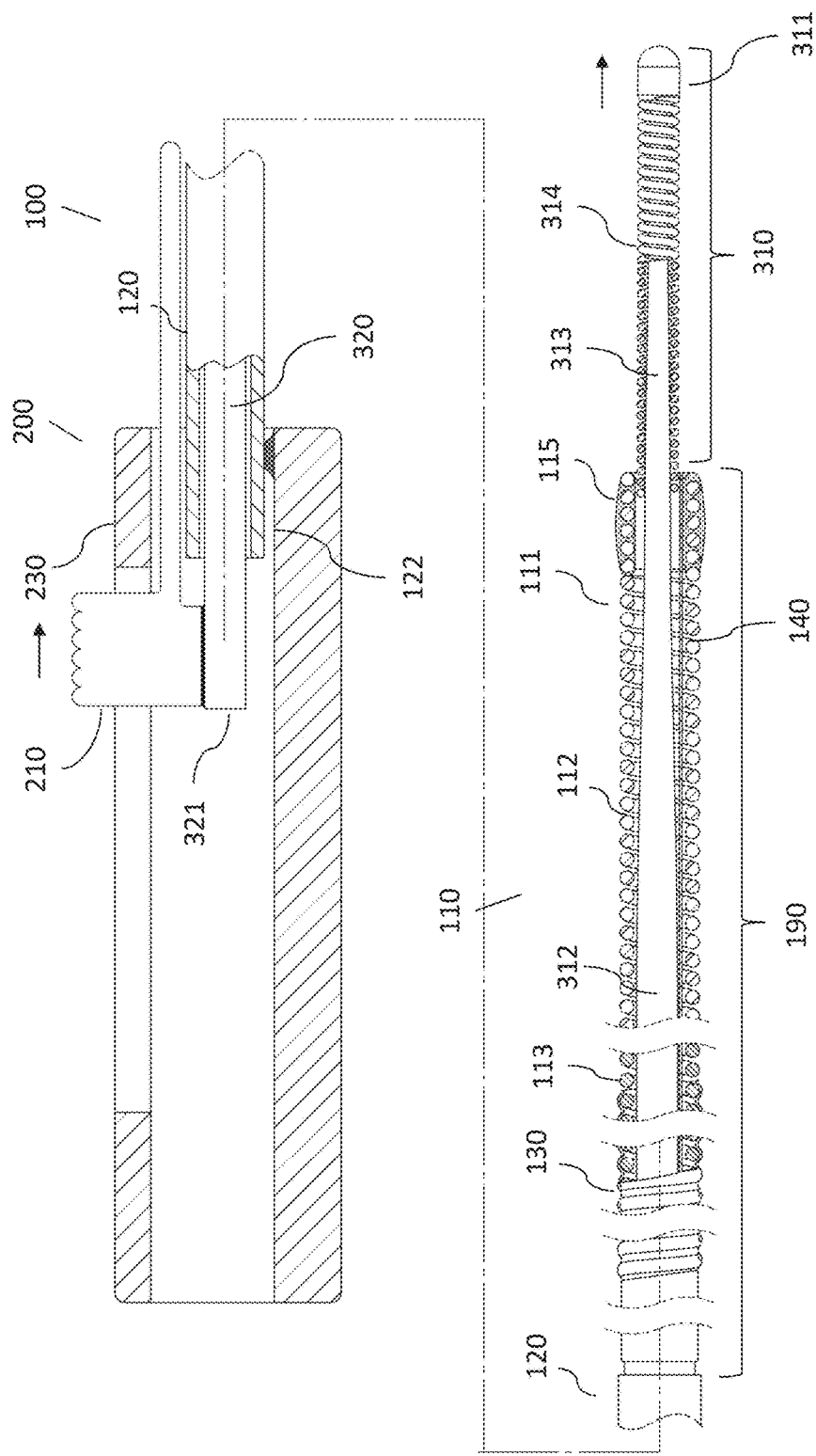
FIG. 6 is a schematic cross section of the Guide Wire of FIG. 1 where the tip of it second inner guide wire is protruding out of the tip of the Guide Wire by manipulating the handle of FIG. 1.

The distal tip (311) of the second guide wire is configured to protrude out of the distal tip (111) of the Guide Wire by manipulating the handle (200). As illustrated in FIG. 6, the distal tip (311) of the second guide wire (300) can be made to protrude out beyond the distal tip of the outer Guide Wire by moving the slider toward the distal end (230) of the handle (200).

The second inner guide wire is of small diameter that can vary from 0.005" to 0.024" depending on the Guide Wire (100) outer diameter. In a preferred embodiment the diameter of at least a distal portion of the second guidewire (300) is smaller than 0.014", and in certain particularly preferred implementations, 0.007"±0.002". This renders the inner guidewire particularly suitable to allow the physician to negotiate the thin micro channels of the proximal cap of a CTO lesion in order to cross through.

Figure 7:
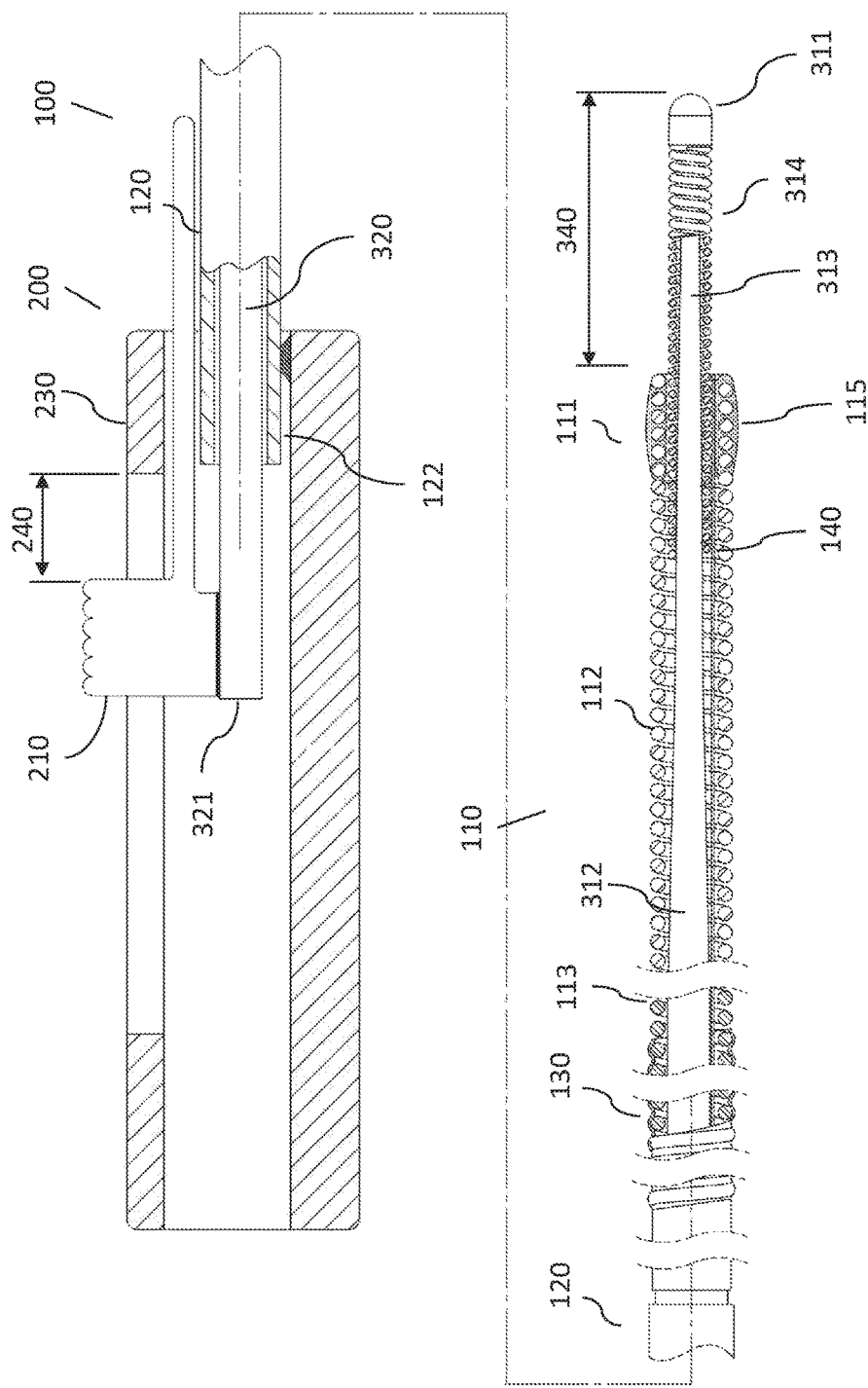
FIG. 7 is a schematic cross section of the Guide Wire of FIG. 1 where the extent of protruding of the second guide wire tip is adjusted by manipulating the handle.

As illustrated in FIG. 7, the extent of protruding (340) of the second guide wire tip (311) is controlled by the distance (240) between the slider (210) and the distal end (230) of the handle (200). By moving the slider (210) the physician can accurately position the tip within the lesion. In addition, the physician can control its stiffness. The tip (311) becomes floppy as the extent of protruding (340) increases. And, in addition, the physician can produce tapping by repeatedly moving the slider (210) back-and-forth.

Figure 8:
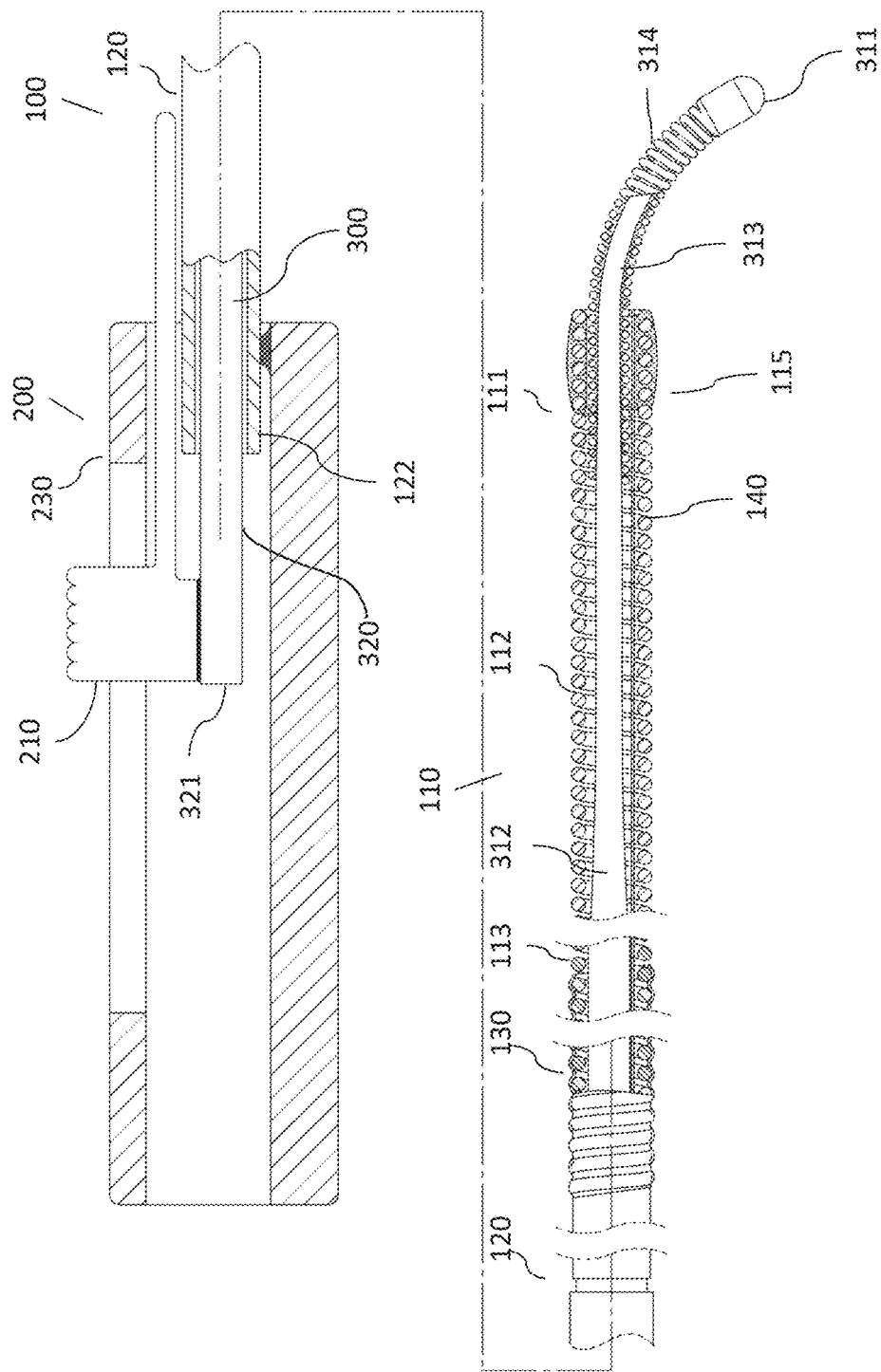
FIG. 8 illustrates a preferred embodiment of the invention, including a second guide wire having a pre-shaped tip such that it curves while it protrudes out of the guide wire tip.

In another preferred embodiment of the invention illustrated in FIG. 8, the second guide wire (300) has a pre-shaped tip (311), such that it curves when it protrudes beyond the outer Guide Wire tip (111).

The embodiments of the guide wire described herein are preferably in the same sizes as a conventional guide wires. Hence the diameter of the Guide Wire (100) is 0.038" or smaller with respect to the conventional sizes of 0.038", 0.024", 0.018" and 0.014".

Balloon dilatation catheters for percutaneous transluminal coronary angioplasty (PTCA) and percutaneous transluminal angioplasty (PTA) are usually intended to be introduced over 0.014" guide wires, referred-to herein as "014 compatible". Therefore, if the Guide Wire (100) of the present invention is intended to facilitate the placement of Balloon dilatation catheters during those procedures, it is of advantage that the Guide Wire is 0.014" or smaller.

It is well accepted among interventional cardiologist physicians that workhorse guide wires (guide wires that are intended to be the first to negotiate the coronary vessels for navigation during PTCA procedures) should be coated with a hydrophilic coating to reduce surface friction to enhance torqueability. It is also well accepted that the distal tips of guide wires that are intended to negotiate CTOs should not be coated because the hydrophilic coating disturbs the tactile sense the physician has regarding the position of the guide wire within the lesion.

It would be of advantage to have a single tool that offers the physician an option to navigate to the CTO lesion with a hydrophilic tip and then negotiate the CTO with an uncoated tip. Therefore, in the preferred embodiment illustrated in FIG. 6, the distal tip (111) of the Guide Wire (100) is coated with hydrophilic coating (160), whereas the distal portion (310) of the second guide wire (300) is un-coated (or may be coated with a coating other than a hydrophilic coating).

Figure 9:
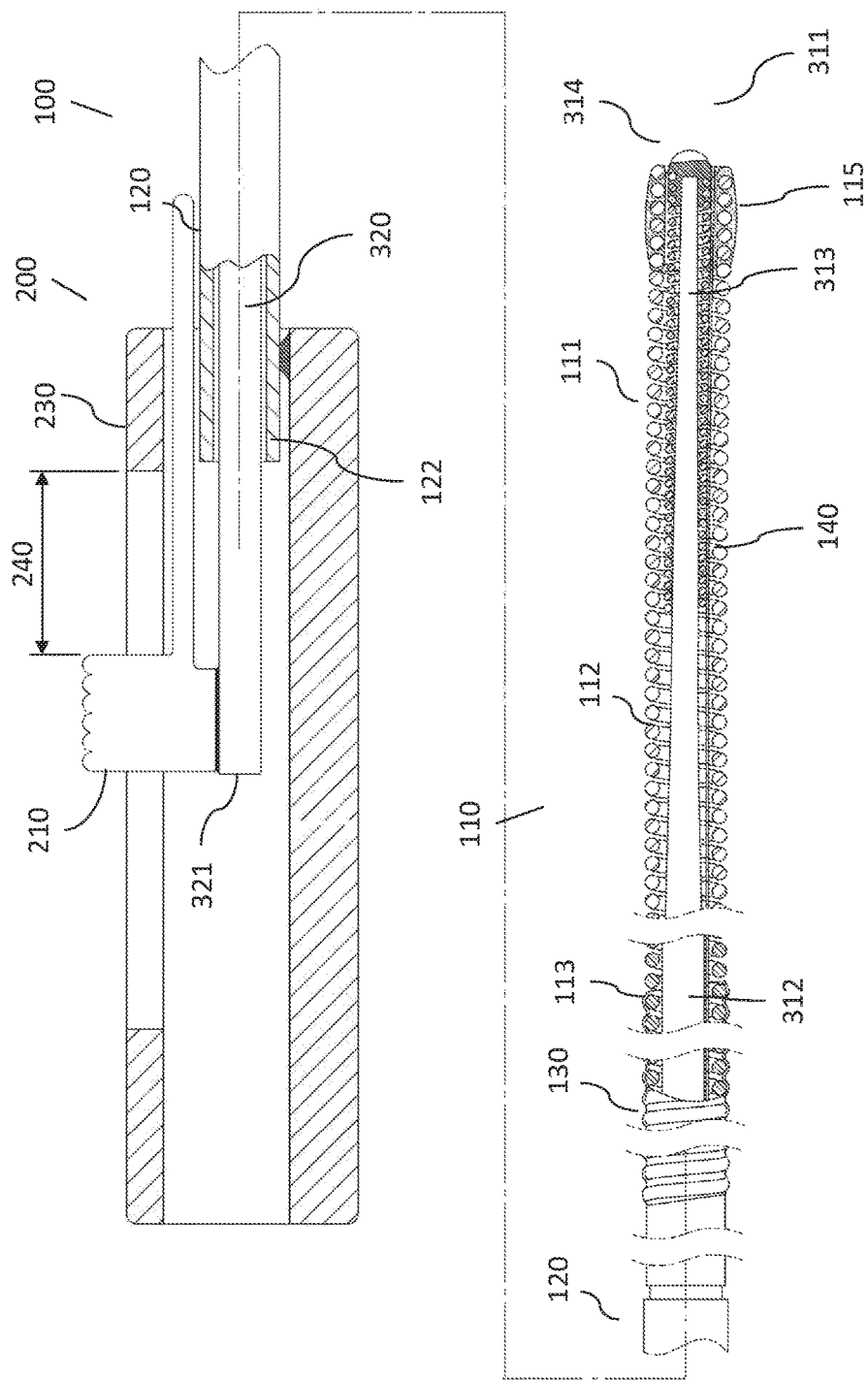
FIG. 9 is a schematic cross section of the Guide Wire of FIG. 1 where the position of the second guide wire tip within the Guide Wire proximal portion is adjusted by manipulating the handle in order to control tip stiffness and curvature.
Figure 10:
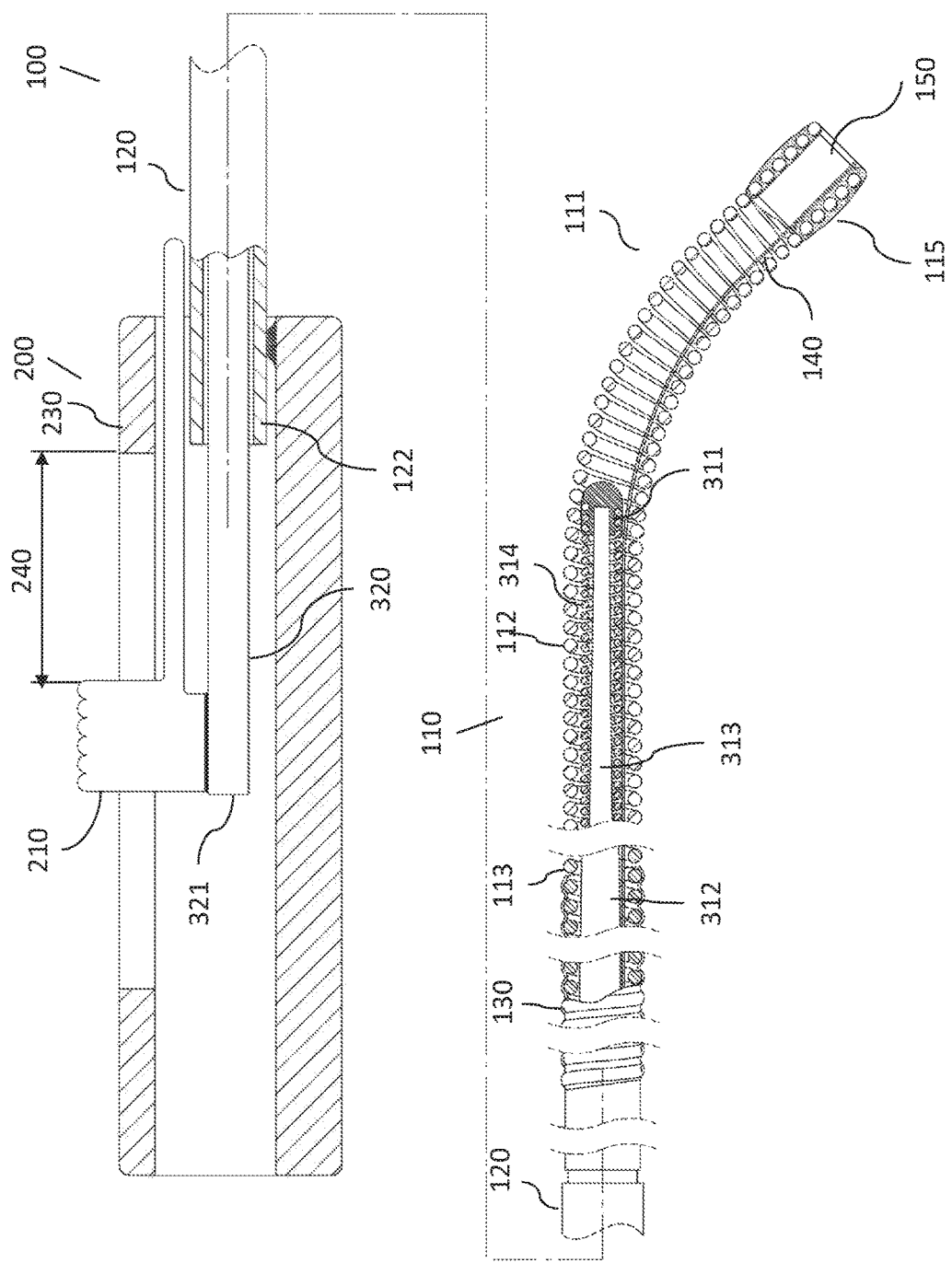
FIG. 10 is another schematic cross section of the Guide Wire of FIG. 1 where the position of the second guide wire tip within the Guide Wire proximal portion is adjusted by manipulating the handle in order to control tip stiffness and curvature.
Figure 11:
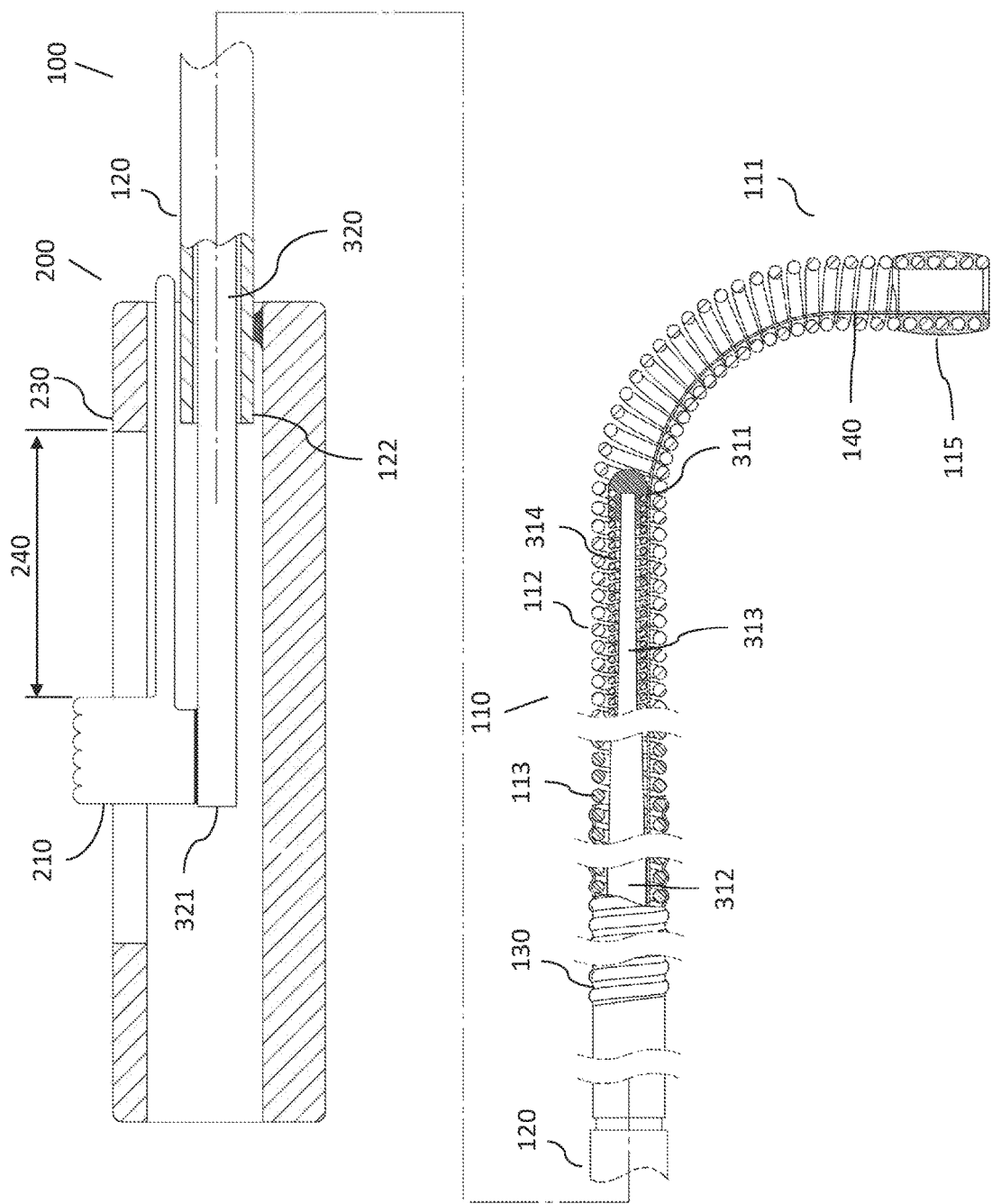
FIG. 11 is also another schematic cross section of the Guide Wire of FIG. 1 where the position of the second guide wire tip within the Guide Wire proximal portion is adjusted by manipulating the handle in order to control tip stiffness and curvature.

As illustrated in FIG. 8, FIG. 9, FIG. 10 and FIG. 11, the position of the distal tip (311) of the second guide wire (300) within the distal portion (110) of the Guide Wire (100) is adjusted by moving the slider (210) with respect to the distal end (230) of the handle (200). FIG. 9 illustrates a position where the tip of the second guide wire is located at the distal end (115) of the tip (111) of the Guide Wire (100). In this position stiffness is at a maximum. In FIGS. 10 and 11, the tip (311) is withdrawn such that a 45 degrees curve or a right-angle curve, respectively, is formed according to the initial shape of the outer Guide Wire tip (111) in a case where the inner guide wire does not induce additional curvature. Additional options providing additional control over the curvature and deflection will be described below with reference to FIGS. 13-16.

By using the slider (210) to displace the tip (311) of the second inner guide wire (300) within the distal portion (110) of the Guide Wire (100), the physician adjusts the stiffness and curvature of the distal tip (111) of the Guide Wire (100) on demand. Hence by using the device of the present invention, the physician can immediately change the characteristics of the Guide Wire he or she is currently using from floppy to stiff and vice versa, with no need to switch between wires.

Figure 4:
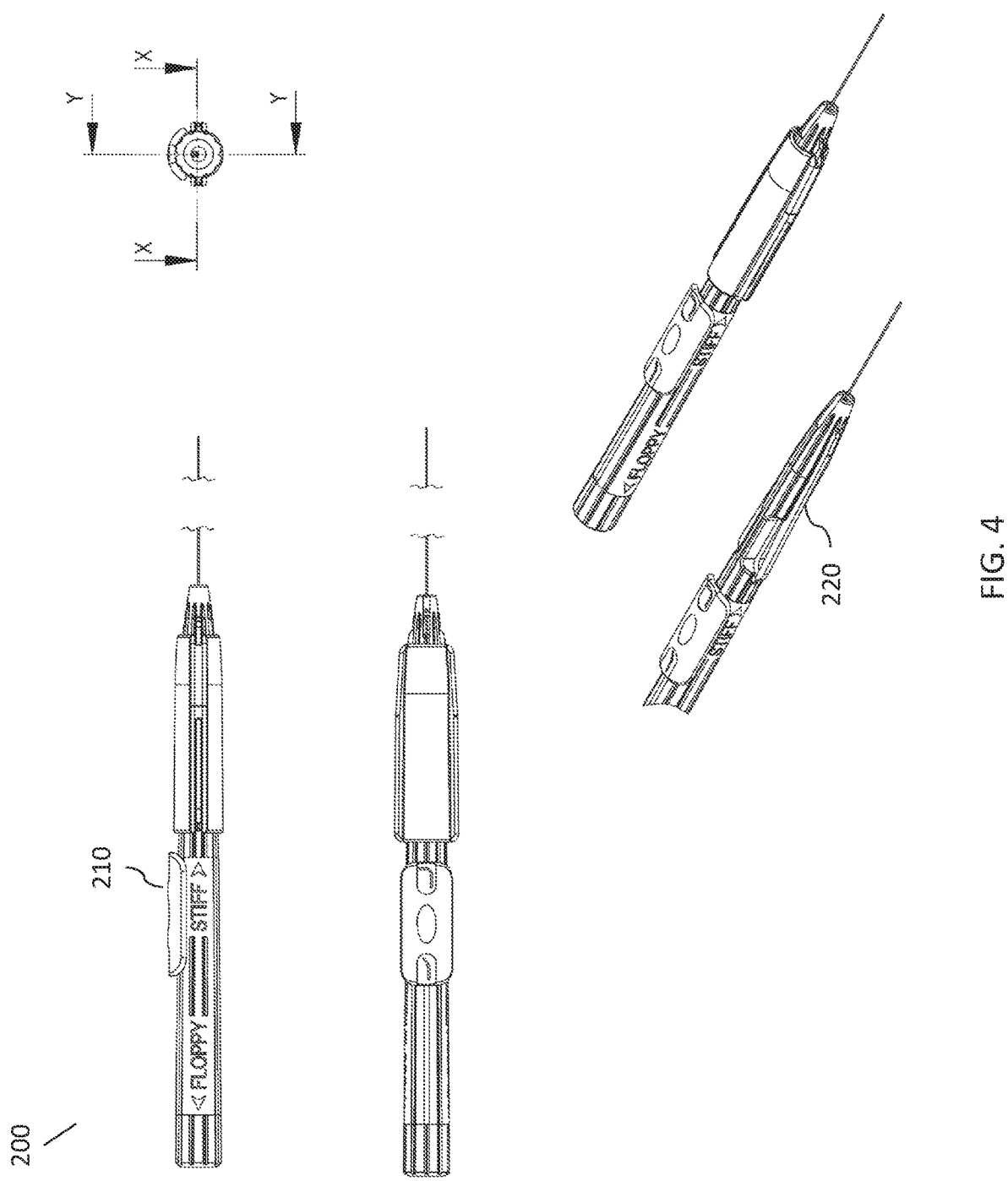
FIG. 4 is a set of views of an example for the handle of FIG. 1
Figure 5:
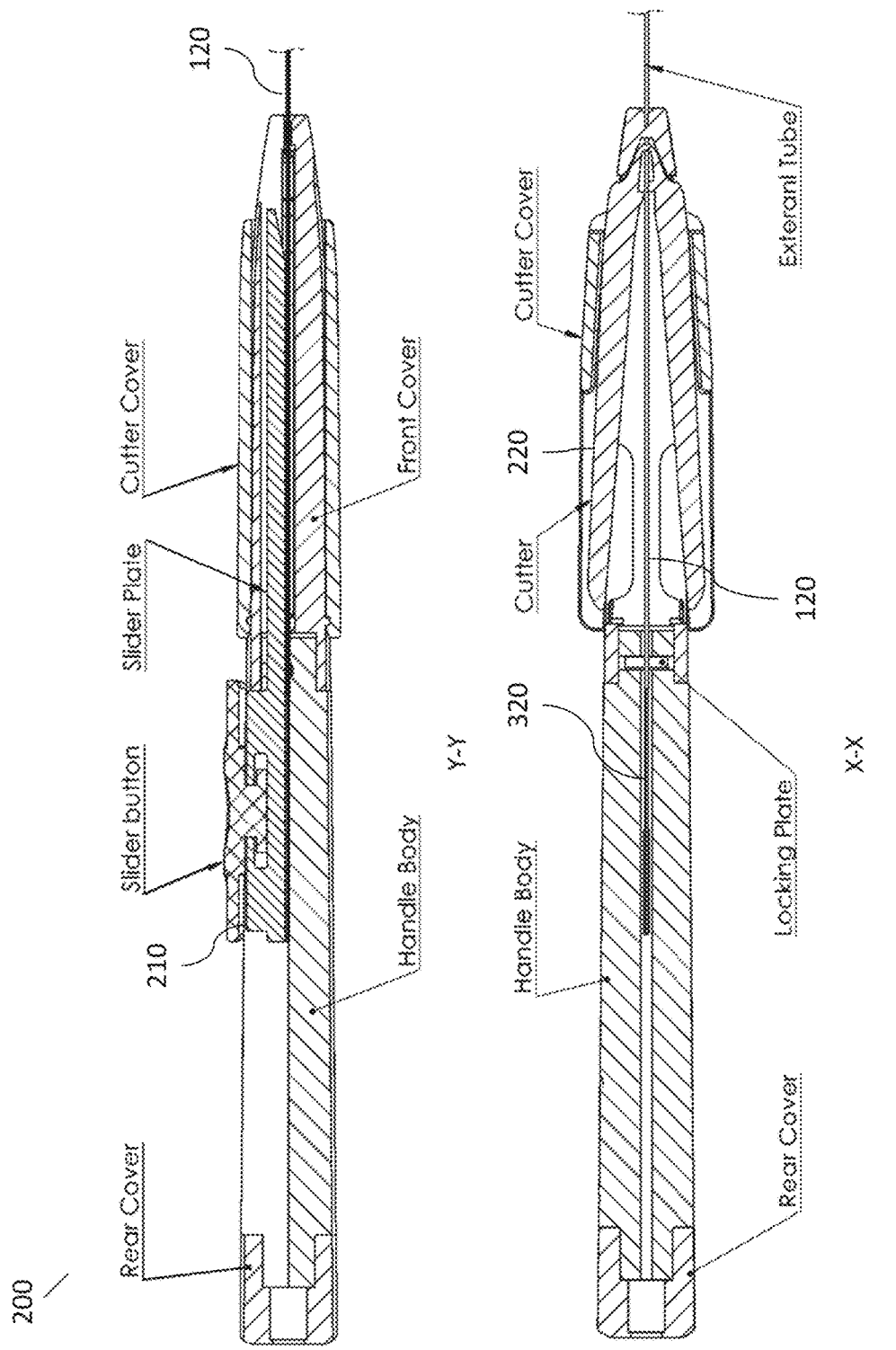
FIG. 5 is a pair of schematic axial cross-sectional views of the handle of FIG. 4.
Figure 12C:
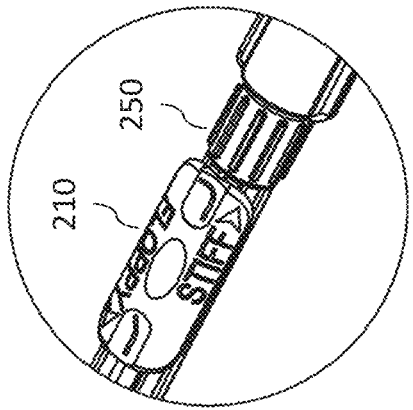
FIGS. 12A-12C are enlarged views of a region of FIG. 12 illustrating a safety ring in a locked position, an unlocked position, and an unlocked position after further advancing of a slider control, respectively.
Figure 12B:
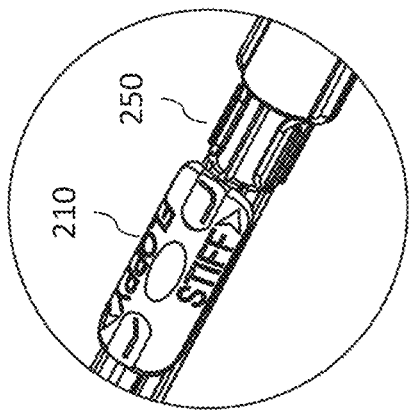
Figure 12A:
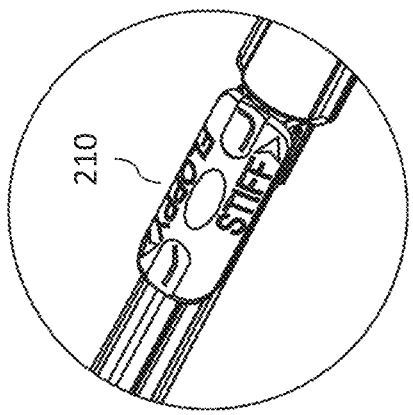
Figure 12:
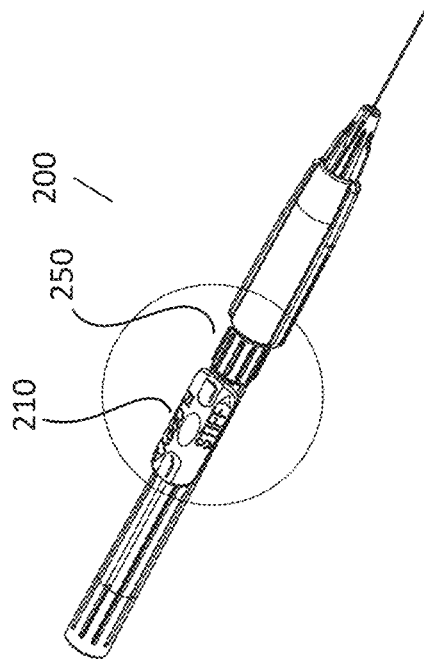
FIG. 12 is a schematic isometric view of a handle of the guidewire of FIG. 1.

In the preferred embodiment illustrated in FIG. 12, the handle of FIG. 4 has a safety ring (250), such that when the slider (210) is stopped by the ring (250), as illustrated in FIG. 12A, the distal tip (311) is advanced to the distal end (115) of the tip (111) of the Guide Wire (100), as illustrated in FIG. 9.

In order to make the tip (311) protrude out of the Guide Wire (100), the physician turns the ring (250), as illustrated in FIG. 12B, to align a slot with the radially-projecting part of slider (210), so that he or she is able to advance the slider (210) toward the distal end (230) of the handle (200), as illustrated in FIG. 12C.

Figure 13:
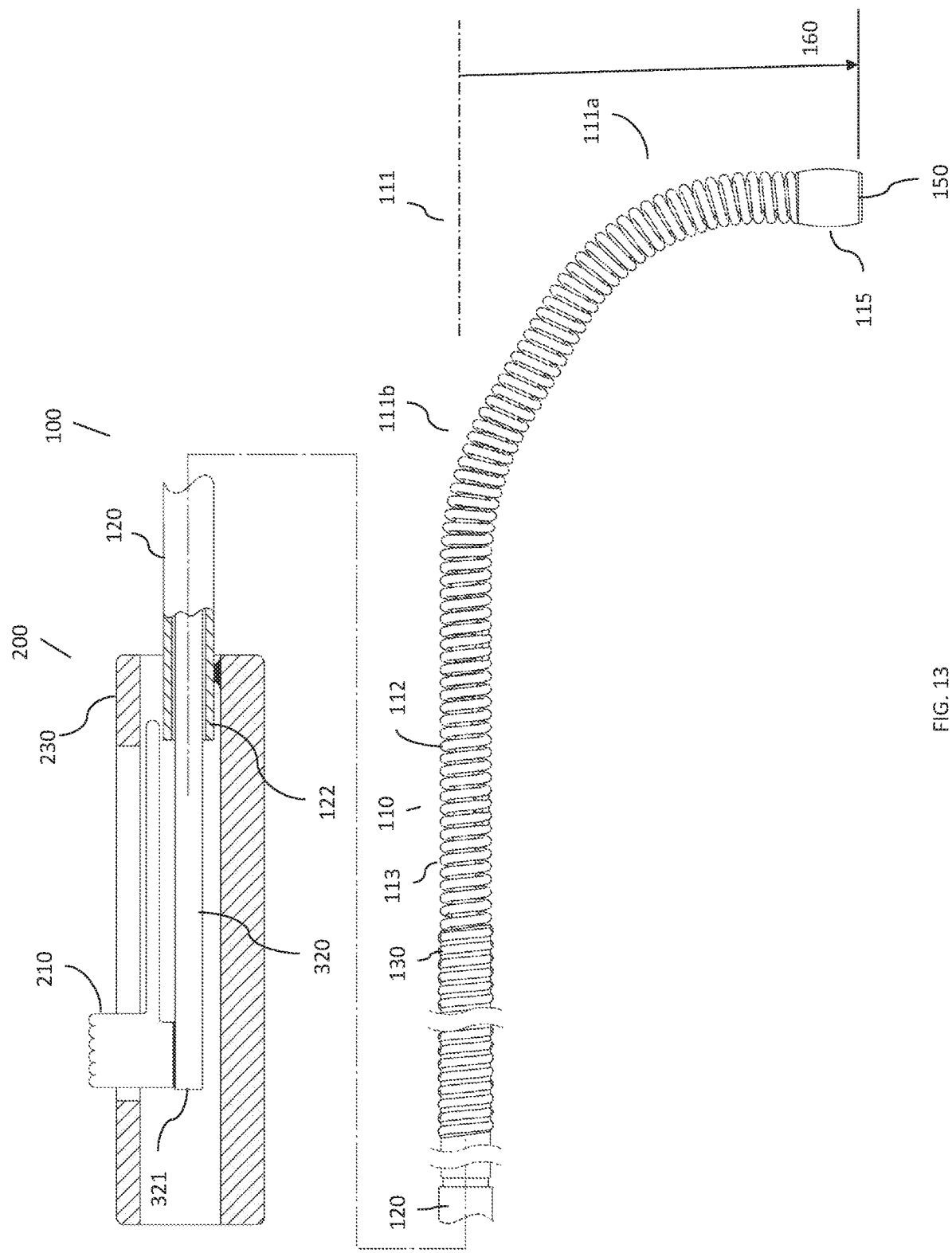
FIG. 13 is a schematic, partially cut-away side view of the guidewire of FIG. 1 in a first state of deflection.
Figure 14:
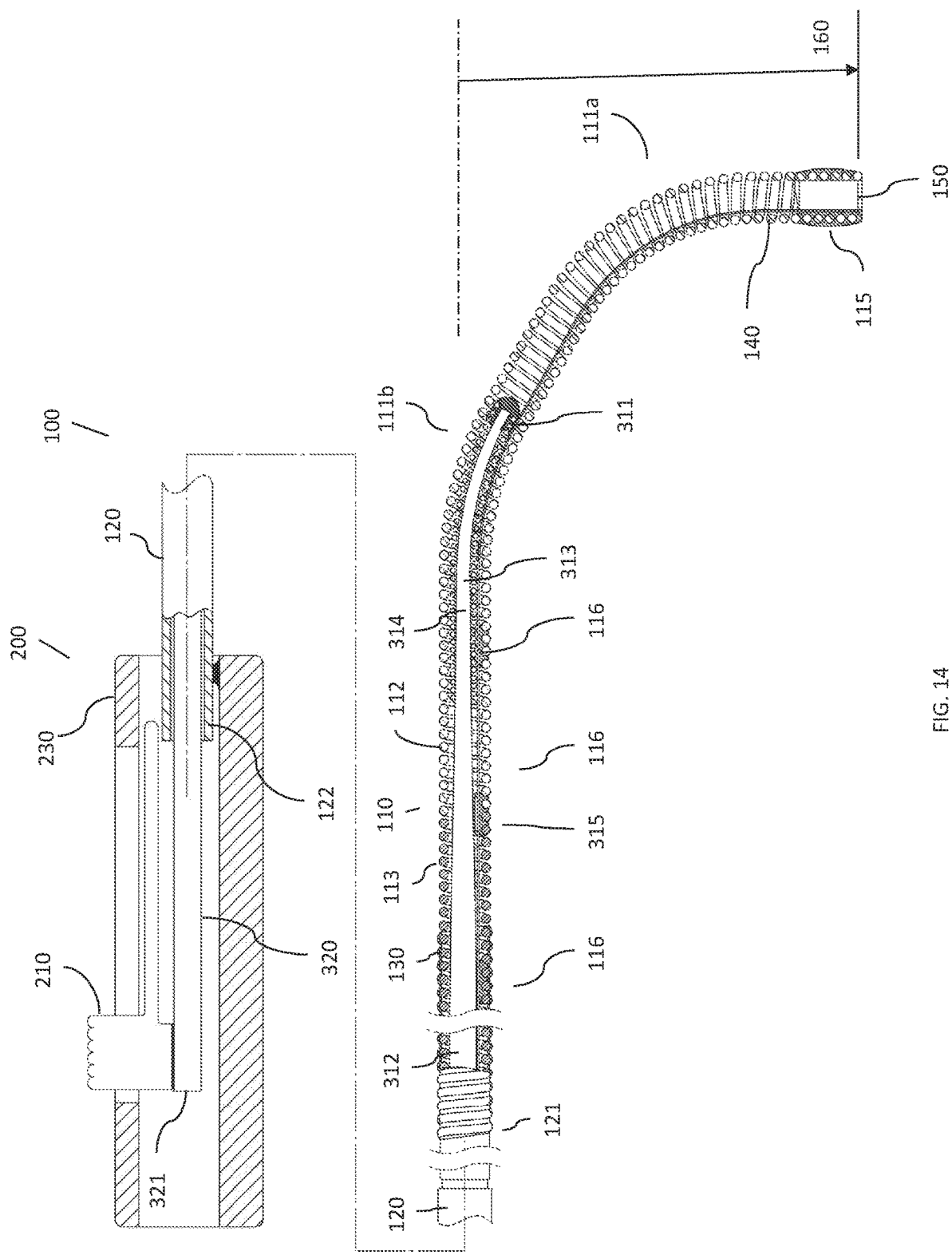
FIG. 14 is a view similar to FIG. 13 in which a distal portion of the guidewire is cut-away along an axial plane.

In a preferred embodiment illustrated in FIG. 13 and FIG. 14, the distal tip (111) is pre-shaped to form a first curve (111a). The distal tip (111) could also be shapeable such that a physician can shape it to form a first curve (111a). As illustrated in FIG. 14, the second inner guide wire (300), extending through the lumen (150) from the handle (200) to the distal tip (111), also has a pre-shaped or user-shapeable distal tip (311).

The distal tip (311) of the second guide wire thus induces a second curve (111b) in the outer guidewire at a corresponding position along the outer guidewire, thereby allowing adjustment of the shape of the tip of the Guide Wire by manipulating the slider (210) of the handle (200). In other words, the presence of the bent tip of inner guidewire within the flexible distal portion of the outer guidewire generates an additional region of deflection which can be displaced relative to the outer guidewire by operating slider (210), thereby adjusting the overall extent, angle and geometry of the curvature of the tip portion of the double guidewire.

Figure 15:
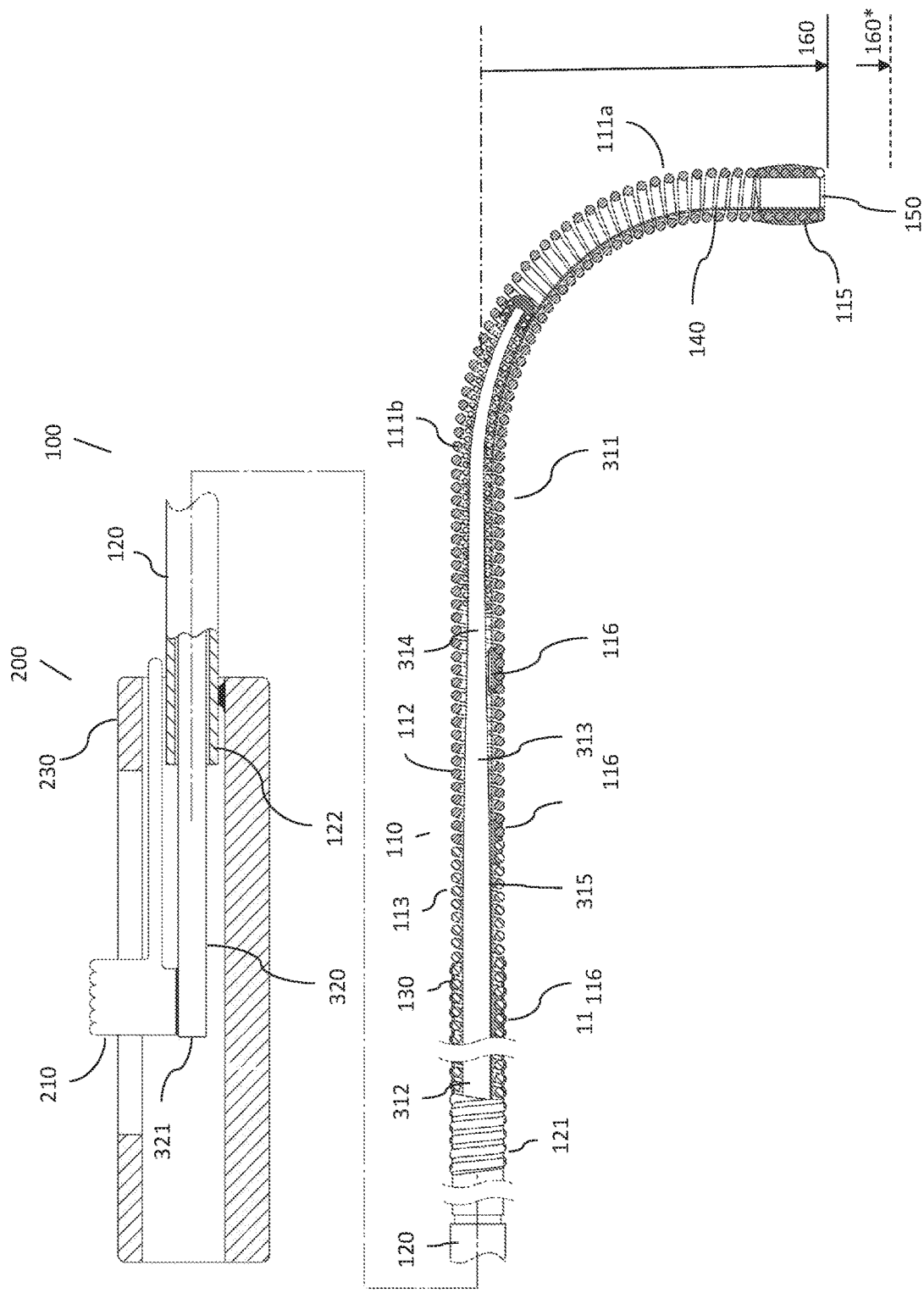
FIG. 15 is a view similar to FIG. 14 showing the guidewire in a second state of deflection.
Figure 16:
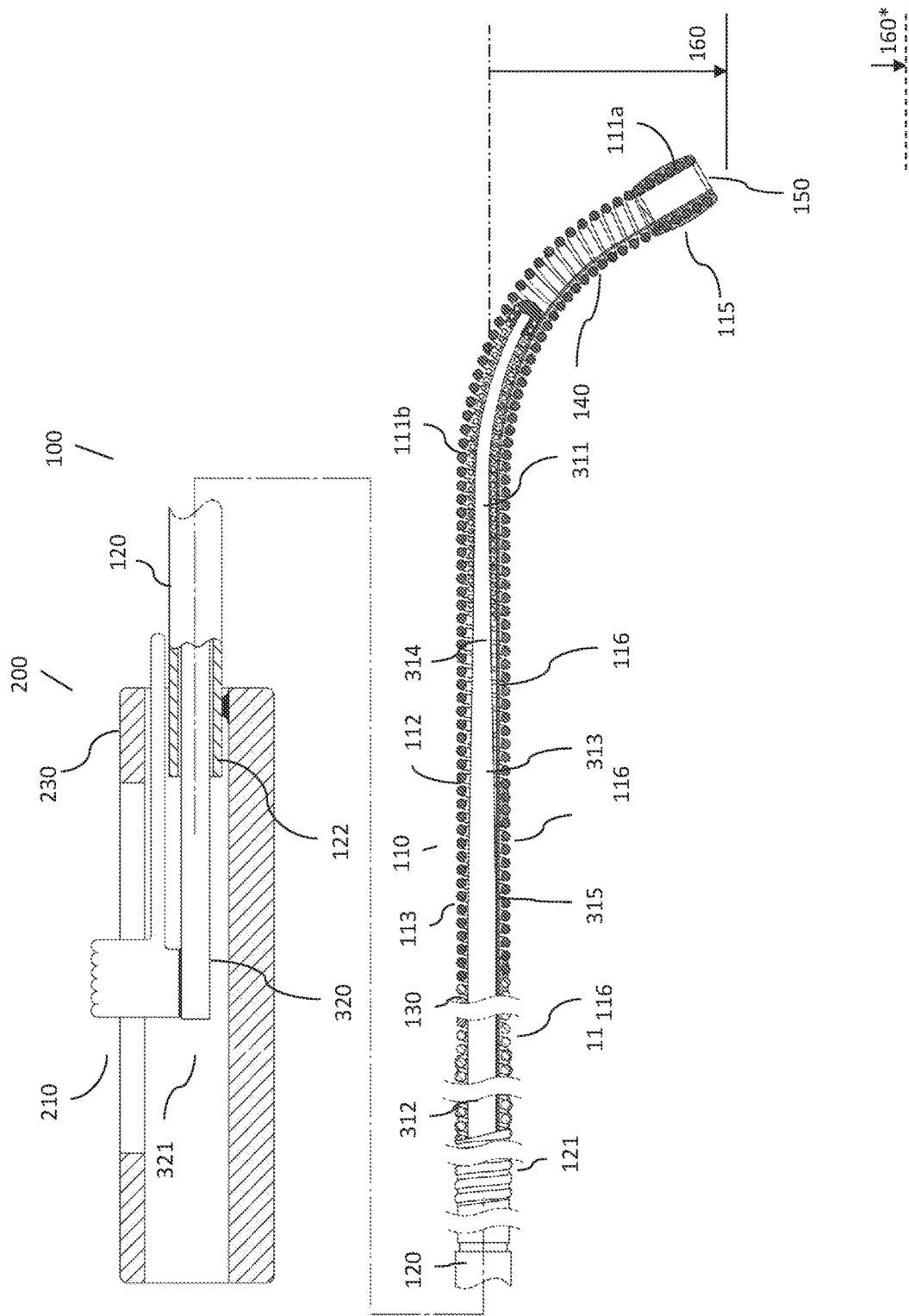
FIG. 16 is a view similar to FIG. 14 showing the guidewire in a third state of deflection.

The effect of this feature is illustrated in FIG. 13, FIG. 14, FIG. 15 and FIG. 16, which illustrate how the radius of curvature and/or length of the tip portion undergoing deflection and/or a total lateral deflection (160) from the axis of the distal tip (111) of the Guide Wire (100) can be adjusted by manipulating the handle: advancing the slider (210) toward the distal end (230) of the handle (200) advances the curved tip (311) within the Guide Wire (100) toward the end (115) of its distal tip (111). This in turn reduces the total lateral deflection (160) of the Guide wire (100) by an adjustable margin (160*), as the distance between the first curve (111a) and second curve (111b) became shorter. More specifically, in FIGS. 13 and 14, each curve (111a) and (111b) corresponds to roughly a 45 degree deflection, and a relatively straight portion lies between the two curves. In FIG. 15, after advancing the inner guidewire slightly relative to the outer guidewire, the two curves are brought close together, resulting in what approximates a continuous curve of roughly 90 degrees, and a reduced overall lateral deflection compared to FIG. 14. Further advancing of the inner guidewire relative to the outer guidewire results in at least partial overlap of the deflected portions of the inner and outer guidewires, so that the overall curvature is less than 90 degrees and the overall lateral deflection is further reduced, as illustrated in FIG. 16. Parenthetically, it should be noted that the principles of operation described with reference to FIGS. 13-16 for adjusting the curvature and deflection of a guidewire correspond to an aspect of the present invention which can be implemented independent of the details of the structure of inner wire (300). Thus, an alternative implementation of this aspect of the present invention provides adjustable curvature and deflection as described with reference to FIGS. 13-16 where the inner element is not implemented as a guidewire with a distal coil but instead is a curvature adjusting element of some other type, such as, for example, a solid wire of suitable diameter with a pre-shaped deflected tip or a user-shapeable tip. In such an embodiment, the adjustment mechanism, such as slider (210), preferably limits motion of the inner curvature adjusting element so as not to be advanced beyond the tip of the outer guidewire.

As illustrated in FIG. 8, by advancing the slider (210) further, the pre-shaped (or user-shaped) curved tip (311) of the second guide wire (300) is made to protrude out of the Guide Wire tip (111), thereby providing the fine-gauge highly-flexible guidewire functionality already discussed above.

The various features of the device of the invention described herein thus provide various improvements to the efficacy of devices for opening CTO lesions and other vascular applications in the coronary and peripheral vascular systems, typically offering time saving and/or reduced risk of perforating the artery compared to conventional techniques.

To the extent that the appended claims have been drafted without multiple dependencies, this has been done only to accommodate formal requirements in jurisdictions which do not allow such multiple dependencies. It should be noted that all possible combinations of features which would be implied by rendering the claims multiply dependent are explicitly envisaged and should be considered part of the invention.

It will be appreciated that the above descriptions are intended only to serve as examples, and that many other embodiments are possible within the scope of the present invention as defined in the appended claims.

What is claimed is:

1. A double guidewire comprising:
   a) a first guidewire comprising an elongated flexible shaft and having a distal portion that terminates in a distal tip, said distal portion of said first guidewire comprising a deflectable helical coil, said first guidewire being a hollow guidewire having a central lumen extending along a length of said first guidewire;
   b) a second guidewire comprising an elongated flexible shaft and having a distal portion that terminates in a distal tip, said distal portion of said second guidewire comprising a deflectable helical coil, said second guidewire being deployed within said central lumen of said first guidewire, wherein the distal tips of the first guidewire and the second guidewire are distinct; and
   c) an adjuster mechanism mechanically linked to a proximal portion of at least said second guidewire, said adjuster mechanism being operable to displace said second guidewire longitudinally relative to said first guidewire between at least:
      i) a first state in which said distal tip of said second guidewire is adjacent to said distal tip of said first guidewire,
      ii) a second state in which at least part of said distal portion of said second guidewire is advanced beyond the distal tip of said first guidewire; and
      iii) a third state in which said distal tip of said second guidewire is withdrawn proximally along said central lumen of said first guidewire so as to leave empty a part of said central lumen of said first guidewire along at least part of said distal portion of said first guidewire;
   wherein a region of said distal portion of each of said first and said second guidewires is preshaped to impart a lateral deflection from a longitudinal axis of the elongated flexible shaft of said first and said second guidewires, respectively,
   wherein, advancing said second guidewire proximally along said central lumen of said first guidewire, from said third state to said first state, results in a reduction of a lateral deflection of said double guidewire, and results in at least partial overlap of the deflected portions of the first and second guidewires.

2. The double guidewire of claim 1, wherein an external surface of said distal portion of said first guidewire is coated with a hydrophilic coating, and wherein an external surface of said distal portion of said second guidewire is not coated with said hydrophilic coating.

3. The double guidewire of claim 1, wherein said first guidewire further comprises a metal strip extending along an inner surface of said helical coil of said distal portion of said first guidewire and permanently attached to said helical coil of said distal portion of said first guidewire at a plurality of spaced-apart locations along said helical coil of said distal portion of said first guidewire.

4. The double guidewire of claim 1, wherein said second guidewire further comprises a tapered metal core extending within said helical coil of said distal portion of said second guidewire and permanently attached to said helical coil of said distal portion of said second guidewire at said distal tip of said second guidewire.

5. The double guidewire of claim 1, wherein an outer diameter of said first guidewire is no greater than 0.014 inch (0.36 mm).

6. The double guidewire of claim 1, wherein an outer diameter of said first guidewire is no greater than 0.038 inch (0.97 mm).

7. The double guidewire of claim 1, further comprising a handle located at a proximal end of said double guidewire, wherein said adjuster mechanism is integrated with said handle.

8. The double guidewire of claim 1, wherein said distal tip of said second guidewire is curved and deflected and displaced longitudinally when it protrudes beyond the distal tip of the first guidewire.

9. A method of performing a surgical procedure on a patient comprising the steps of:
   a) providing a double guidewire comprising:
      a) a first guidewire comprising an elongated flexible shaft and having a distal portion that terminates in a distal tip, the distal portion of the first guidewire comprising a deflectable helical coil, the first guidewire being a hollow guidewire having a central lumen extending along a length of the first guidewire;
      b) a second guidewire comprising an elongated flexible shaft and having a distal portion that terminates in a distal tip, the distal portion of the second guidewire comprising a deflectable helical coil, the second guidewire being deployed within the central lumen of the first guidewire, wherein the distal tips of the first guidewire and the second guidewire are distinct; and c) an adjuster mechanism mechanically linked to a proximal portion of at least the second guidewire, the adjuster mechanism being operable to displace the second guidewire longitudinally relative to the first guidewire between at least:
  i) a first state in which the distal tip of the second guidewire is adjacent to the distal tip of the first guidewire,
  ii) a second state in which at least part of the distal portion of the second guidewire is advanced beyond the distal tip of the first guidewire; and
  iii) a third state in which said distal tip of said second guidewire is withdrawn proximally along said central lumen of said first guidewire so as to leave empty a part of said central lumen of said first guidewire along at least part of said distal portion of said first guidewire;

wherein a region of the distal portion of each of said first and said second guidewires is preshaped to impart a lateral deflection from a longitudinal axis of the elongated flexible shaft of each of said first and said second guidewires, respectively, and wherein a region of the distal portion adjacent to the distal tip of each of the first and second guidewires having a lateral deflection, a deflected portion of the first guidewire having a first length;

b) introducing the double guidewire into a bodily lumen of the patient and navigating the double guidewire within the bodily lumen to reach a target location; and c) selectively displacing the second guidewire relative to the first guidewire, via the adjuster mechanism, so as to locate the deflected portion of the first guidewire and a second deflected portion of the second guidewire longitudinally relative to each other, thereby imparting to the double guidewire a lateral deflection extending for a second length, the second length being greater than the first length, to facilitate navigation of the double guidewire within the bodily lumen.

10. The method of claim 9, further comprising selectively displacing the second guidewire relative to the first guidewire so that the distal portion of the second guidewire extends beyond the distal tip of the first guidewire.

11. The method of claim 9, further comprising advancing along the double guidewire an "014-compatible" over-the-wire device selected from the group consisting of: an angioplasty balloon and an expandable stent.

12. The method of claim 9, further comprising rotating at least the first guidewire about its longitudinal axis.

13. The method of claim 9, wherein the bodily lumen comprises a blood vessel.

14. The method of claim 9, wherein the displacement of the second guidewire within the first guidewire generates an additional region of deflection.

15. The method of claim 9, wherein the displacement of the second guidewire adjusts an overall extent, angle and geometry of the curvature of a distal tip portion of the double guidewire.

* * * * *